United States Patent [19]

Eibl et al.

[11] Patent Number: 4,510,084

[45] Date of Patent: Apr. 9, 1985

[54] METHOD OF PRODUCING AN ANTITHROMBIN III-HEPARIN CONCENTRATE OR ANTITHROMBIN III-HEPARINOID CONCENTRATE

[75] Inventors: Johann Eibl; Ernst Hetzl; Yendra Linnau, all of Vienna, Austria

[73] Assignee: Immuno Aktiengesellschaft für chemisch-medizinische Produkte, Vienna, Austria

[21] Appl. No.: 611,639

[22] Filed: May 18, 1984

[30] Foreign Application Priority Data

May 20, 1983 [AT] Austria ................................. 1859/83

[51] Int. Cl.³ .................... C07G 7/00; A61K 37/64; A61K 31/725; C08B 37/10
[52] U.S. Cl. ................................. 260/112 B; 424/101
[58] Field of Search .................... 260/112 B; 424/101, 424/177, 183

[56] References Cited

U.S. PATENT DOCUMENTS

| | | | |
|---|---|---|---|
| 3,842,061 | 10/1974 | Andersson et al. | 260/112 B |
| 3,920,625 | 11/1975 | Andersson et al. | 260/112 B |
| 4,087,415 | 5/1978 | Bick et al. | 260/112 B |
| 4,388,232 | 6/1983 | Eibl et al. | 260/112 B |
| 4,446,126 | 5/1984 | Jordan | 424/101 X |
| 4,465,623 | 8/1984 | Chanas et al. | 260/112 B |

FOREIGN PATENT DOCUMENTS

| | | |
|---|---|---|
| 48893 | 4/1982 | European Pat. Off. |
| 148297 | 5/1981 | German Democratic Rep. |
| 2061287 | 5/1981 | United Kingdom |

OTHER PUBLICATIONS

Rosenberg, Chemistry & Physiology of the Human Plasma Proteins, H. Bing, Editor, Pergamon Press (1979), pp. 353–368.
Rosenberg et al., J. of Biol. Chem., vol. 248, No. 18, (1973), pp. 6490–6505.
Thrombosis Research, vol. 5, No. 4 (1974), pp. 439–452 (Miller-Anderson et al.).

*Primary Examiner*—Howard E. Schain
*Attorney, Agent, or Firm*—Burns, Doane, Swecker & Mathis

[57] ABSTRACT

In a method of producing an antithrombin III-heparin or an antithrombin III-heparinoid concentrate, heparin or heparinoid is added to human plasma or to antithrombin III containing plasma fractions to form an antithrombin III-heparin or antithrombin III-heparinoid complex, the complex thus formed is adsorbed on an anion exchanger, and eluted with a salt solution; then the antithrombin III-heparin or antithrombin III-heparinoid complex contained in the eluate is separated from salts and undesired proteins, and the resulting product is loyphilized.

12 Claims, No Drawings

METHOD OF PRODUCING AN ANTITHROMBIN III-HEPARIN CONCENTRATE OR ANTITHROMBIN III-HEPARINOID CONCENTRATE

The invention relates to a method of producing an antithrombin III-heparin or antithrombin III-heparinoid concentrate.

It is known that antithrombin III forms a complex together with heparin or heparinoids, which complex has pharmaceutically valuable properties; in particular, the presence of these complexes in the preparation and storage of concentrates of highly effective coagulation factors and other plasma proteins with biological activity suppresses enzymatically caused protein changes which may have undesired side reactions on the patient. Also concentrates of antithrombin III have a similar effect. Further pharmaceutically valuable properties of these products are their efficacy relative to thromboembolism in case of a congenital antithrombin III deficiency as well as in high-risk patients in whom an antithrombin III-decline occurs upon heparin therapy.

In U.S. Pat. No. 4,388,232 the formation of an antithrombin III-heparin complex is disclosed, in that heparin is added to human citrated plasma or to purified antithrombin III. The mixture is added to Factor VIII containing fractions for stabilizing purposes. An isolation of the complex does not take place in this instance.

In the published European patent application Ser. No. 0 048 898 the production of an antithrombin III-heparin complex is disclosed, in which pre-purified antithrombin III and heparin are adsorbed on immobilzed lectin, the excessive heparin is removed by washing and the complex is eluted with carbohydrate solutions. This leads to a problem with the leakage of the ligand, since the lectins used have mitogenic effects. Therefore, the therapeutic application of a product thus produced is risky.

In the publication "The Chemistry and Physiology of the Human Plasma Proteins" by R. D. Rosenberg, page 353, Ed. H. Bing, Pergamon Press, 1979, Rosenberg describes the production of the complex of purified antithrombin III and heparin, wherein the complex is separated from excessive heparin by gel filtration and isolated. Furthermore, according to Rosenberg the complex can be dissociated into its components by gel filtration in the presence of a 3 M NaCl solution.

Insofar as antithrombin III-heparin complexes have hitherto been produced as such, i.e., as pure substances, this was done for analytical purposes mainly. Gel filtration or affinity chromatography with toxic ligands, such as lectins, do not constitute suitable methods for the production of therapeutically useful products.

The invention aims at avoiding these disadvantages and difficulties and has as its object enabling the provision of antithrombin III-heparin or antithrombin III-heparinoid complex concentrates on a production scale, in order to obtain products suitable for the use as therapeutics.

The invention departs from a method of producing an antithrombin III-heparin or antithrombin III-heparinoid concentrate, wherein human plasma or antithrombin III-containing plasma fractions are mixed with heparin or heparinoid under formation of an antithrombin III-heparin or antithrombin III-heparinoid complex, and which is characterized in that the antithrombin III-heparin or antithrombin III-heparinoid complex is adsorbed on an anion exchanger, the adsorbate is eluted by a salt solution, the eluate is treated so as to purify the antithrombin III-heparin or antithrombin III-heparinoid complex from salts and undesired proteins and the product obtained is brought into stable form by lyophilization.

Contrary to the production methods initially mentioned, the measures taken according to the invention are very simple and can be carried out with good yields. A partial denaturation of the antithrombin III does not take place with the method according to the invention. A very good heparin binding capability of the antithrombin III is obtained, and the heparin has a high affinity to antithrombin III, although none of the two partners need be purified before. As anion exchangers, such based on cross-linked dextran gels (e.g., DEAE-Sephadex, QAE-Sephadex) or DEAE-cellulose may be used. Suitably, the adsorbate is washed before the elution.

According to an advantageous embodiment, the eluate is treated with protein precipitating agents, such as ammonium sulfate, in a concentration which suffices to precipitate the antithrombin III-heparin or antithrombin III-heparinoid complex, whereupon the precipitate is dissolved, the solution is thermally inactivated and the product is lyophilized thereafter. The thermal treatment for inactivating infection germs possibly present can be effected by heating to 60° C. for a period of 10 hours.

With this working method the solution containing the antithrombin III-heparin or antithrombin III-heparinoid complex after the thermal inactivation step may additionally be treated with a protein precipitating agent, i.e. in a concentration which suffices to remove the undesired proteins but leaves the complex itself in solution.

A preferred embodiment or variant of the method according to the invention relates to the production of an antithrombin III concentrate from the complex concentrates produced in the manner disclosed and is characterized in that a solution enriched with the purified complex, in particular the solution present before the lyophilization step, is treated with immobilized protamine, wherein the complex is cleaved and heparin is bound to the immobilized protamine, whereupon the supernatant containing the antithrombin III is brought into stable form by lyophilization.

The recovery of the antithrombin III from the complex, with heparin remaining bound, is superior to the methods of isolating antithrombin III hitherto known, since the complex can be obtained in a simple manner and with an excellent yield. The leakage of the ligands is not important in this case, since protamine is clinically used for neutralizing heparin and thus is unharmful. Isolating methods for antithrombin III hitherto known (cf., e.g., R. D. Rosenberg et al., J. Biol. Chem. 248, 6490 (1973)) recommended adsorption on Al(OH)$_3$, elution with ammonium phosphate, further purification via gel filtration, ion exchange chromatography and isoelectric focussing.

In U.S. Pat. No. 4,087,415, for the production of antithrombin III there is provided an adsorption on Al(OH)$_3$, elution with phosphate/EDTA, further purification by fractionation with Pluronic or polyethylene glycol.

Finally, in Thromb. Res. 5, 439 (1974), a method of obtaining antithrombin III by affinity chromatography is disclosed by M. Miller-Andersson et al., wherein antithrombin III is adsorbed on heparin agarose and a further purification is effected via ion exchange chromatography and gel filtration.

The method according to the invention shall now be explained in more detail by way of the following examples:

EXAMPLE 1

Production of antithrombin III-heparin complex from plasma

To 100 l of plasma there were added $8.10^6$ U of heparin after the removal of the cryoprecipitate, and it was stirred for 30 min at $+4°$ C. After 100 g of DEAE-Sephadex A 50 had been stirred in, stirring was continued for further 2 hours at $+4°$ C. The gel was separated by Büchner filters and washed with 2 l of a phophate-citrate buffered, isotonic saline solution having a pH of 7.5 for removing accompanying proteins. The washed gel was suspended in 2.2 l of the above-mentioned buffer, and a conductivity of 42 mS/cm was adjusted by adding solid NaCl. After stirring for one hour at $+4°$ C. a separation by Büchner filters was carried out and it was washed a second time with 0.7 l of a phophate and citrate buffered saline solution having a conductivity of 42 mS/cm.

From the combined eluates the antithrombin III-heparin complex was precipitated by adding 1.4 kg of ammonium sulfate and adjusting the pH to 5.5. The ammonium sulfate concentration of 430 g/l used herein corresponds to an 80% saturation of the solution. After stirring for one hour at $+4°$ C. the precipitate was separated by filtration and dissolved in 1.5 l of distilled water together with 13.5 g of NaCl and 221 g of $Na_3$ citrate . $2H_2O$.

The pH was adjusted to 7.5 and it was heated for 10 hours at $60°$ C. for inactivating any hepatitis viruses possibly present.

The pasteurized product was dialyzed against 50 l of isotonic saline solution, and for a further purification 303 g of ammonium sulfate were added per 1 l at a pH of 7.0. The ammonium sulfate concentration of 270 g/l used herein corresponds to a 50% saturation of the solution. After stirring for 45 min at $+4°$ C., the precipitate was separated by centrifugation and discarded.

The supernatant was dialyzed against 100 l of a citrate buffered isotonic saline solution and concentrated by ultrafiltration to an antithrombin III content of 50 U/ml.

After dialysis against a citrate buffered isotonic saline solution it was sterile-filtered, filled into bottles and lyophilized.

The enzymatic activities of antithrombin III and heparin were tested in the following manner:

Enzymatic activity of antithrombin III:

The activity was based on a standard preparation which had been calibrated against antithrombin III plasma human (1.Int. R. P 72/1). With this standard preparation a calibration curve was determined on which the samples to be tested were read off.

The dilution of the samples and of the standard to activities between 0.0125 and 0.0625 U/ml was effected by means of a buffer solution having the following composition:

| | |
|---|---|
| 3.03 g of Tris | |
| 10.8 g of NaCl | per 1 l, pH 8.4 |
| 1.4 g of Na—EDTA | |
| 3,000 U of heparin | |

Pipetting pattern:
(a) 0.1 ml of sample was heated to $37°$ C.
(b) 0.1 ml of thrombin (12 IU/ml) was added, and it was incubated for 3 min at $37°$ C.
(c) 0.1 ml of a 1.2 mM solution of TH-1 (2 AcOH.H-D-CHG-Ala-Arg-pNA) was added
(d) after exactly 1 min at $37°$ C. the reaction was stopped by adding 1.0 ml of 20% acetic acid
(e) the extinction was measured at 405 nm.

Enzymatic activity of heparin:

The activity was based on a standard preparation which had been calibrated against the 3. Int. Stand. heparin 65/69. With this standard preparation a calibration curve was determined on which the samples to be tested were read off.

The dilution of the samples and of the standard to activities of 0.001 to 0.5 IU/ml was effected by means of a buffer solution having the following composition:

| | |
|---|---|
| 6.06 g of Tris | |
| 18.12 g of NaCl | per 1 l, pH 8.3 |
| 2.79 g of Na—EDTA | |

Pipetting pattern:
(a) 0.2 ml of sample and 0.2 ml of heparin-free antithrombin III (3 U/ml) were incubated for 20 min at room temperature and for 3 to 5 min at $37°$ C.
(b) 0.2 ml of thrombin (20 IU/ml) were added, and it was incubated for 1.5 min at $37°$ C.
(c) 0.2 ml of a 1.2 mM solution of Th-1 were added
(d) after exactly 1 min at $37°$ C. the reaction was stopped by adding 0.2 ml of 50% glacial acetic acid
(e) the extinction was measured at 405 nm.

For the final product obtained according to Example 1 there resulted a heparin content of from 5 to 7 heparin units per unit of antithrombin III.

EXAMPLE 2

Production of antithrombin III from antithrombin III-heparin complex

For this working method an immobilized protamine, a so-called protamine gel, is required. Such gels may be produced in various manners. In the following, two methods are listed.

Method 1: Protamine-Sepharose 1 l of a cross-linked 6% agarose gel (Sepharose Cl-6B) is suspended in 2 l of a 1 M $Na_2CO_3$ solution and activated with a solution of 100 g of BrCN in 100 ml of acetonitrile at a pH of from 11.0 to 11.5 and a temperature of from $5°$ to $10°$ C.

Subsequently it is washed four times with 3 l each of a 0.2 M $NaHCO_3$ solution, and finally with 3 l of a borate-buffered saline solution having a pH of 9.5. The BrCN-activated gel is stirred over night with 1 l of the above-mentioned borate-saline solution to which 20 g of protamine sulfate were added, at a pH of 9.5 and a temperature of $+4°$ C.

After blocking of the residual active groups with 1 l of a 1 M ethanol amine solution (2 h at room temperature), it is washed alternately three times each with 3 l each of a $NaHCO_3$-buffered saline solution having a pH of 8.5 and an acetate-buffered saline solution having a pH of 4.0.

Before being used for removing heparin, the protamine gel is equilibrated with a Tris and citrate-buffered saline solution having a pH of 8.0.

Method 2: Protamine-Eupergit

To 5 g of Oxiran acrylic resin (Eupergit C) there was added a solution of 400 mg of protamine sulfate in 20 ml of 1 M potassium phosphate having a pH of 9.5 and allowed to stand for 16 hours at room temperature. After washing with water, 1 M NaCl solution and 0.01 M phosphate solution, the residual reactive groups were blocked with 70 ml of a 5% solution of beta-mercapto ethanol (16 h, at room temperature). Finally, it was washed five times with 80 ml df water each. Before being used for removing heparin, it is equilibrated as in Method 1.

The antithrombin III-heparin complex produced according to Example 1 was dissolved or the solution obtained after dialysis was used. To 1 l each of this dialyzed solution, 1 g of Tris was added, the pH was adjusted to 8.0, and 15 ml of the protamine-gel produced according to Method 1 were added. After stirring over night, the gel was separated by filtration; the main amount of the heparin-free antithrombin III was in the adsorption supernatant.

For increasing the yield of antithrombin III, the gel was washed with Tris and citrate-buffered saline solutions of increasing ionic strengths. The adsorption supernatant and the heparin-free washing supernatants were combined for isolating antithrombin III and were lyophilized for concentration. The powder thus obtained was suspended in 1 ml of distilled water per 1 g and dialyzed against a citrate-buffered isotonic saline solution. After dialysis, it was diluted to an antithrombin III content of 50 U/ml, it was sterile-filtered, filled into bottles and lyophilized.

The enzymatic analysis gave a heparin content of less than 0.5 U of heparin per 1 U of antithrombin III.

EXAMPLE 3

Production of an antithrombin III-heparinoid complex

To 1 l of plasma there were added 3 g of the heparinoid pentosan polysulfate sodium salt (Polyanion SP 54), whereupon it was stirred at +4° C. for 30 min. After 2.5 g of DEAE-Sephadex A 50 had been stirred in, the stirring was continued for further 2 hours at +4° C. The gel was separated by Büchner filters and washed twice with 200 ml each of a phosphate and citrate-buffered isotonic saline solution for removing accompanying proteins. The washed gel was suspended in 100 ml of the abovementioned buffer, and a conductivity of 60 mS/cm was adjusted by adding solid saline. After stirring for 1 hour at +4° C. it was separated by Büchner filters and the antithrombin III-SP 54-complex was obtained.

The further processing of the eluate to the final product was carried out as described in Example 1.

The enzymatic analysis showed a heparinoid content corresponding to an activity of from 2 to 3 U of heparin per 1 U of antithrombin III. What we claim is:

1. In a method of producing an antithrombin III-heparin concentrate or an antithrombin III-heparinoid concentrate, which method includes adding heparin or heparinoid to human plasma or to antithrombin III-containing plasma fractions under formation of an antithrombin III-heparin complex or an antithrombin III-heparinoid complex, the improvement comprising adsorbing the antithrombin III-heparin complex or the antithrombin III-heparinoid complex formed on an anion exchanger thus forming an adsorbate, eluting said adsorbate with a salt solution thus forming an eluate, separating said antithrombin III-heparin or antithrombin III-heparinoid complex contained in said eluate from salts and undesired proteins, and lyophilizing the resulting product so as to bring it into stable form.

2. A method as set forth in claim 1, further comprising the step of washing said adsorbate before eluting said adsorbate.

3. A method as set forth in claim 1, wherein said eluate is treated with protein precipitating agents, in a concentration sufficing to form an antithrombin III-heparin-complex-precipitate or an antithrombin III-heparinoid-complex-precipitate, said precipitate is dissolved so as to form a solution, said solution is thermally inactivated and subsequently lyophilized.

4. A method as set forth in claim 3, wherein said protein precipitating agents are comprised of ammonium sulfate.

5. A method as set forth in claim 3, wherein after thermally inactivating said solution, said solution containing said antithrombin III-heparin complex or said antithrombin III-heparinoid complex is further treated with a protein precipitating agent in a concentration sufficing to remove undesired proteins but leaving said antithrombin III-heparin complex or said antithrombin III-heparinoid complex in solution.

6. A method as set forth in claim 5, wherein said protein precipitating agent for further treating said antithrombin III-heparin complex or antithrombin III-heparinoid complex is comprised of ammonium sulfate.

7. A method of producing an antithrombin III concentrate from said antithrombin III-heparin concentrate or from said antithrombin III-heparinoid concentrate produced as set forth in claims 1, wherein a purified solution enriched with said antithrombin III-heparin complex or said antithrombin III-heparinoid complex, in particular the solution purified from salts and undesired proteins as present to lyophilizing, is treated with immobilized protamine so as to cleave said antithrombin III-heparin complex or said antithrombin III-heparinoid complex and bind said heparin or heparinoid to said immobilized protamine, a supernatant containing said antithrombin III forming, and wherein said supernatant containing said antithrombin III is lyophilized so as to bring it into stable form.

8. A method of producing an antithrombin III concentrate from said antithrombin III-heparin concentrate or from said antithrombin III-heparinoid concentrate produced as set forth in claim 2, wherein a purified solution enriched with said antithrombin III-heparin complex or said antithrombin III-heparinoid complex, in particular the solution purified from salts and undesired proteins as present to lyophilizing, is treated with immobilized protamine so as to cleave said antithrombin III-heparin complex or said antithrombin III-heparinoid complex and bind said heparin or heparinoid to said immobilized protamine, a supernatant containing said antithrombin III forming, and wherein said supernatant containing said antithrombin III is lyophilized so as to bring it into stable form.

9. A method of producing an antithrombin III concentrate from said antithrombin III-heparin concentrate or from said antithrombin III-heparinoid concentrate produced as set forth in claim 3, wherein a purified solution enriched with said antithrombin III-heparin complex or said antithrombin III-heparinoid complex, in particular the solution purified from salts and undesired proteins as present to lyophilizing, is treated with immobilized protamine so as to cleave said antithrombin III-heparin complex or said antithrombin III-heparinoid complex and bind said heparin or heparinoid to said immobilized protamine, a supernatant containing said antithrombin III forming, and wherein said supernatant containing said antithrombin III is lyophilized so as to bring it into stable form.

10. A method of producing an antithrombin III concentrate from said antithrombin III-heparin concentrate or from said antithrombin III-heparinoid concentrate produced as set forth in claim 4, wherein a purified solution enriched with said antithrombin III-heparin complex or said antithrombin III-heparinoid complex, in particular the solution purified from salts and undesired proteins as present to lyophilizing, is treated with immobilized protamine so as to cleave said antithrombin III-heparin complex or said antithrombin III-heparinoid complex and bind said heparin or heparinoid to said immobilized protamine, a supernatant containing said antithrombin III forming, and wherein said supernatant containing said antithrombin III is lyophilized so as to bring it into stable form.

11. A method of producing an antithrombin III concentrate from said antithrombin III-heparin concentrate or from said antithrombin III-heparinoid concentrate produced as set forth in claim 5, wherein a purified solution enriched with said antithrombin III-heparin complex or said antithrombin III-heparinoid complex, in particular the solution purified from salts and undesired proteins as present to lyophilizing, is treated with immobilized protamine so as to cleave said antithrombin III-heparin complex or said antithrombin III-heparinoid complex and bind said heparin or heparinoid to said immobilized protamine, a supernatant containing said antithrombin III forming, and wherein said supernatant containing said antithrombin III is lyophilized so as to bring it into stable form.

12. A method of producing an antithrombin III concentrate from said antithrombin III-heparin concentrate or from said antithrombin III-heparinoid concentrate produced as set forth in claim 6, wherein a purified solution enriched with said antithrombin III-heparin complex or said antithrombin III-heparinoid complex, in particular the solution purified from salts and undesired proteins as present to lyophilizing, is treated with immobilized protamine so as to cleave said antithrombin III-heparin complex or said antithrombin III-heparinoid complex and bind said heparin or heparinoid to said immobilized protamine, a supernatant containing said antithrombin III forming, and wherein said supernatant containing said antithrombin III is lyophilized so as to bring it into stable form.

* * * * *

UNITED STATES PATENT AND TRADEMARK OFFICE
CERTIFICATE OF CORRECTION

PATENT NO. : 4,510,084

DATED : April 9, 1985

INVENTOR(S) : EIBL et al.

It is certified that error appears in the above-identified patent and that said Letters Patent is hereby corrected as shown below:

On the title page:

Delete under Foreign Patent Documents, first reference, "48893", and insert -- 48898 --.

Signed and Sealed this

Twenty-ninth Day of July 1986

[SEAL]

Attest:

DONALD J. QUIGG

Attesting Officer

Commissioner of Patents and Trademarks